United States Patent [19]

Mathews et al.

[11] Patent Number: 4,963,349
[45] Date of Patent: Oct. 16, 1990

[54] PERMANENT WAVE SOLUTION

[75] Inventors: Roger A. Mathews, Newbury Park; Edward R. Moore, Canoga Park; David W. Cannell, Los Angeles, all of Calif.

[73] Assignee: Redken Laboratories, Inc., Canoga Park, Calif.

[21] Appl. No.: 253,860

[22] Filed: Oct. 4, 1988

[51] Int. Cl.$^5$ ................................................. A61K 7/09
[52] U.S. Cl. ....................................... 424/72; 514/772
[58] Field of Search ........................... 424/72; 514/772

[56] References Cited

U.S. PATENT DOCUMENTS

| | | | |
|---|---|---|---|
| 2,389,755 | 11/1945 | Baker | 424/71 |
| 3,039,934 | 6/1962 | Whitman et al. | 424/72 |
| 3,240,672 | 3/1966 | Eckstrom | 424/71 |
| 4,243,659 | 1/1981 | Balingit et al. | 424/70 |

Primary Examiner—Merrell C. Cashion, Jr.
Assistant Examiner—Susan S. Rucker
Attorney, Agent, or Firm—Christie, Parker & Hale

[57] ABSTRACT

An aqueous permanent wave solution employing one or more compounds for cleaving keratin interprotein disulfide bonds is enhanced by including a biocompatible 1,3-alkyldiol. Preferably from two to seven percent by weight of 2-ethyl-1,3-hexanediol or 1,3-butanediol is employed. Such compositions provide a useful neutral permanent wave solution employing ammonium thioglycolate, the first permanent wave solution with a pH in the same acidic range as the isolectric point of hair, or a five minute permanent wave with either an acid or alkaline solution.

21 Claims, No Drawings

PERMANENT WAVE SOLUTION

BACKGROUND OF THE INVENTION

This invention relates to a composition for permanent waving of hair, which stimulates the rate of reaction and final curl efficiency while leaving the hair soft and lustrous.

Various compounds are used in permanent waving solutions because of their reactions with the keratin protein chains in the hair, which cleave the interprotein disulfide bonds. This softens the fibers of hair so that a wave can be formed. The wave can then be set by reversing the reactions with an oxidant such as hydrogen peroxide or sodium bromate. Suitable compounds include salts and esters of thioglycolic acid or thiolactic acid, beta-mercaptoethylamine, thioglycerol, cysteine, and sodium bisulfite. Thioglycolic acid salts are the most commonly used in commercial salon waving solutions, although some of the other materials find use in specific applications.

The principal salts and esters of thioglycolic acid used in commercial permanent wave solutions are ammonium thioglycolate (ATG), monoethanolamine thioglycolate (MEATG) and glyceryl monothioglycolate (GMTG). GMTG is an excellent nucleophile at a pH in the range of from 7 to 8 and has been the thioglycolate of choice for permanent wave solutions having a neutral pH. It would be desirable, however, to employ ATG in a neutral permanent wave solution since GMTG is an expensive chemical which must be packaged separately from other parts of the composition, which adds to its expense and imposes an extra difficulty in usage. Further, GMTG is purported to be an irritant or sensitizer which may limit its use for some individuals.

There are also times when it is desirable to have a "non-ammonia" wave solution where MEATG is the sole waving agent in the solution. These are difficult products due to their tendency to react very slowly with the hair and often give poor hair condition due to the difficulty in "reading" the progress of the wave by test curl procedures commonly practiced in the art. This often results in operator error and overprocessing of the permanent wave.

Further, it is desirable to accelerate curl formation and stabilization in an alkaline permanent wave solution so that the time required for processing can be reduced. It is desirable to have a solution that reproducibly processes hair in about five minutes instead of the twenty minutes typically required. The desirability of a five minute salon wave is apparent; the operators may be able to give twice as many permanent waves in a day as they can at present. A patron may be able to easily get a permanent wave during lunch hour. This has not previously been possible without using extremely strong solutions of thioglycolate and alkalinity which may severely compromise hair condition.

The isoelectric point of hair is about pH 3 to 5. It would be desirable to have a permanent wave solution having a pH in that range. Some sodium bisulfite permanent wave solutions have had a pH as low as about 6, but no truly acid solutions near the isoelectric point of hair are known. It would be desirable to have permanent wave solutions which have a pH approximately the same as the hair.

BRIEF SUMMARY OF THE INVENTION

There is, therefore, provided in practice of this invention a permanent wave solution which has at least one compound which will cleave interprotein disulfide bonds, and a biocompatible 1,3-alkyldiol.

Preferably, the solution comprises a conventional aqueous permanent wave solution with from two to seven percent by weight of 2-ethyl-1,3-hexanediol or 1,3-butanediol. Such solutions permit "five minute" permanent waves with mild conditions, permit use of ATG in a neutral pH solution, provide a truly acid permanent wave at a pH near the isoelectric point of hair, and generally enhance curl efficiency.

DETAILED DESCRIPTION

This invention provides a breakthrough in permanent wave composition technology. It demonstrates a true synergism between a class of compounds that are essentially ineffective by themselves and the effective compounds that cleave interprotein bonds in the hair. The new class of compounds useful in permanent wave solutions are the 1,3-alkyldiols. They do not seem to have any significant effect on hair when used alone, but when combined with compounds that are effective, they greatly enhance the cleavage reactions without introducing such strong conditions that the hair itself is easily damaged. Thus, enhanced curling efficiency is obtained under mild conditions.

This results in a commercially acceptable "lunch hour" permanent wave where the permanent wave lotion can be applied for as little as five minutes on all types of hair, instead of the twenty minutes conventionally used. This is also a boon to the salon operators who can increase productivity enormously without risk to their patrons. Surprisingly, it also permits formulation of the world's first truly acid permanent wave solution having a pH as low as the natural pH of the hair. Salon permanent wave solutions have traditionally been alkaline with a pH in the order of 9, or at best have been near neutral by use of costly ingredients or at the sacrifice of curling efficiency. The desirability of an effective truly acid solution is suggested by the trade's jargon of referring to the neutral solutions as "acid". It is particularly surprising that a solution can be made that not only has a pH in the range of from 3 to 5, but also provides a "five minute" permanent.

The preferred permanent wave solution contains 2-ethyl-1,3-hexanediol, which can be used in virtually any standard permanent wave solution for stimulating the rate of reaction and curl efficiency of the solution. It is believed that this material and other 1,3-alykldiols stimulate the cleavage of cystine and exert a powerful effect at the level of protein rearrangement. These compounds are not normally regarded as useful for cleaving interprotein disulfide bonds, thus, they are used in practice of this invention in combination with compounds that are effective in such cleavage. For example, enhanced curl efficiency is obtained with a broad variety of known cleavage agents, including the thioglycolates, such as ATG, MEATG, and GMTG, thiolactates, mercapto compounds, and thioglycerol. The 1,3-alkyldiols do not appear to be helpful with the weaker cleaving agents cysteine and sodium bisulfite. The reason for this is not known. However, other mild agents for cleaving the interprotein disulfide bonds may also have enhanced activity and become suitable for use in permanent wave compositions. It is found that the action of the conventional permanent wave thioglycolates is enhanced significantly throughout their useful pH range. For example, testing shows that 2-ethyl-1,3-hexanediol enables formulation of an ammonium thioglycolate permanent wave solution at pH 7 which is equal to or slightly better than standard glycerylmonothioglycolate permanent wave solutions. Without the addition of the 1,3-alkyldiol the waving action of the ATG solution at this neutral pH is not commercially acceptable. Extraordinarily strong solutions would be needed to get the desired curl efficiency, with undue risk to the patron's hair.

Table I presents the results of half-head salon permanents comparing a pH 7.0 solution containing GMTG with an otherwise identical solution containing ATG and five percent of 2-ethyl-1,3-hexanediol. In the salon tests, the hair on one-half of the subject's head was processed with the prior GMTG solution and the other half was processed with the ATG solution containing the 1,3-diol. This test involved nine subjects and the average scores represent ratings by licensed cosmetologists who evaluated the permanent wave on each half of the head at the end of the procedure and two weeks later. The ratings are on a scale of one to ten, with ten being the best.

TABLE I

| Salon Performance Test | | |
|---|---|---|
| Parameter | ATG & 1,3-Diol | GMTG |
| Curl Pattern | 9.2 ± 1.0 | 9.0 ± 0.0 |
| Wet Combability | 9.0 ± 0.6 | 8.7 ± 0.5 |
| Dry Texture | 8.3 ± 0.5 | 8.3 ± 0.5 |
| Sheen | 8.0 ± 0.0 | 8.3 ± 0.5 |
| Two Weeks Post-Perm | | |
| Curl Pattern | 9.0 ± 1.1 | 8.8 ± 1.2 |

It is found that the range of concentration of 1,3-alkyldiol useful in practice of this invention is from two percent to seven percent by weight and preferably the material is present in the range of from four to six percent by weight. Table II sets forth the effect of concentration of 2-ethyl-1,3-hexanediol on curl efficiency. The solutions tested used ammonium thioglycolate as the permanent waving agent at a pH of 7.0. Except for the 1,3-diol concentration, the solutions were identical. In all cases the hair was processed for twenty minutes at 50° C.

A conventional measure of permanent waving efficiency was employed. In such a test a swatch of hair is wrapped in a serpentine path on rows of pegs and treated with permanent waving solution. After a desired period of exposure to the reducing permanent wave solution, the hair is rinsed and set with an oxidizer in a conventional manner. The wet hair is removed from the pegs and the length of a portion of the waved swatch is compared with the length of a similar portion of the rows of pegs (e.g., five wave lengths). Efficiency is indicated as a percentage based on the increased length of the waved specimen as compared with the distance between the respective pegs. An efficiency of 100 percent represents hair that did not change dimension upon removal from the pegs. Generally speaking, increasing efficiency is desired up to about 85 percent, above which damage to the hair may occur. Generally speaking, it is believed that a permanent wave must be about 70 to 75% efficient by this measure to be commercially viable.

TABLE II

| Effect of 1,3-Diol Concentration (ATG cleavage agent, pH 7.0) | |
|---|---|
| % 2-ethyl-1,3-hexanediol | % Efficiency |
| 0% (Control) | 58% |
| 1% | 63% |
| 2% | 68% |
| 3% | 72% |
| 4% | 77% |
| 5% | 86% |
| 6% | 77% |
| 7% | 72% |

The data in Table III are similar for a different permanent wave solution. In these tests the permanent wave solution contained ammonium thioglycolate as the waving agent at a pH of 9.2. The hair was processed for ten minutes at room temperature.

TABLE III

| Effect of 1,3-Diol Concentration (ATG waving agent, pH 9.2) | |
|---|---|
| % 2-ethyl-1,3-hexanediol | % Efficiency |
| 0% (Control) | 65% |
| 1% | 67% |
| 2% | 67% |
| 3% | 72% |
| 4% | 72% |
| 5% | 77% |
| 6% | 72% |
| 7% | 70% |

Table IV shows the effect of 2-ethyl-1,3-hexanediol on permanent waving efficiency for a variety of hair processing parameters. In each case identical solutions were used except for the presence or absence of five percent of 2-ethyl,1,3-hexanediol. It can be seen that the curl efficiency increased significantly for alkaline or neutral solutions, for various thioglycolates, and at both room temperature and 50° C.

TABLE IV

| Effect of 2-ethyl-1,3-hexanediol on Waving Efficiency | | | | | |
|---|---|---|---|---|---|
| | | | | % Efficiency | |
| Waving Agent | pH | Time | Temp. | No 2-ethyl-1,3-hexanediol | With 5% 2-ethyl-1,3-hexandiol |
| ATG | 9.2 | 5 min. | 50° C. | 64% | 72% |
| ATG | 9.2 | 10 min. | R.T. | 65% | 77% |
| MEATG | 9.2 | 30 min. | R.T. | 67% | 79% |
| MEATG | 9.2 | 5 min. | 50° C. | 64% | 75% |
| GMTG | 7.0 | 15 min. | 50° C. | 73% | 82% |
| ATG | 7.0 | 15 min. | 50° C. | 72% | 83% |
| ATG | 7.0 | 20 min. | 50° C. | 58% | 86% |
| GMTG | 8.0 | 15 min. | R.T. | 61% | 79% |

Thus, the 1,3-diol improves curl efficiency in solutions using ATG alone, MEATG alone or GMTG alone. It is found that it also improves performance in solutions using a combination of ATG and MEATG. A solution using MEATG alone is desirable since it permits a totally non-ammonia permanent wave, and such products have not otherwise been commercially practical. Either the ATG or MEATG solution with 2-ethyl-1,3-hexanediol at a pH of about 9 reproducibly produces good results in five minutes of processing time on all types of hair. A particularly preferred composition employs a combination of seven percent ATG and two percent MEATG to provide a five minute permanent wave. Normal or resistant hair requires the application of heat (up to 50° C.), whereas tinted, frosted or bleached hair is processed at room temperature.

The 1,3-diols also enhance the performance of GMTG in permanent wave solutions, however, need for this more expensive ingredient may be avoided because of the enhanced results obtained with the less costly thioglycolates. A desirable composition, however, comprises GMTG stimulated by addition of a 1,3-alkanediol, such as 2-ethyl-1,3-hexanediol, with a pH in the range of from 7 to 8. Such a solution can be used for a five minute permanent wave by application of heat (50° C.) or a longer period without heating. There is also an enhanced effect when the salts of thiolactic acid or thioglycerol are used for cleaving the interprotein disulfide bonds.

Significantly, the composition also enhances the permanent wave obtained with beta-mercaptoethylamine (also known as cysteamine). Tests have shown that excellent results are obtained with this material at a pH of about 4.1 to 4.2 when the solution also contains 2-ethyl-1,3-hexanediol. Without the 1,3-diol, the solution does not work at all. This finding provides the first permanent wave solution having a pH the same as the natural isoelectric point of hair, that is, in the range of from 3 to 5. Particularly surprising is that the solution can provide better than 70% curling efficiency with only five minutes of treatment at 50° C.

The proportion of ATG in a permanent wave solution, such as may be used at a neutral pH, is in the range of from three to twelve percent by weight. Similarly the proportion of MEATG in a permanent wave solution is also in the range of from three to twelve percent by weight. Either ATG or MEATG or both may be used in alkaline pH ranges. If both ATG and MEATG are used, the total is also in the range of from three to twelve percent. Similar ranges are appropriate for the usable thiolactates, mercapto compounds, esters of thioglycolic acid and the like.

It is the 1,3-diol arrangement that appears to be effective. Thus, for example, 1,3-butanediol has been found to be effective, although the 2-ethyl-1,3-hexanediol material is preferred. Other 1,3-alkyldiols that are biocompatible and safe to use on the scalp may also be used. The useful 1,3-alkyldiols have sufficient water solubility to be retained in a permanent wave solution. It appears that the higher molecular weight 1,3-alkyldiols are more effective than lower molecular weight 1,3-alkyldiols. This is believed to be due to the higher hydrophobicity of the higher molecular weight materials. It is postulated that in the milieu of the hair wetted with the waving solution, the 1,3-alkyldiol preferentially locates at the hair surface and stimulates the protein cleavage reactions and protein rearrangements. The higher molecular weight materials would be more likely to do so. The 2-ethyl-1,3-hexanediol is particularly preferred since it is relatively inexpensive, readily available, non-toxic, sufficiently soluble to stay in aqueous solution and quite effective.

Other diols such as the 1,2-diols, 2,4-diols and 1,6-diols have been found not to be functional. Compounds that are not effective include glycerine, propylene glycol, ethylene glycol, hexylene glycol, polyethylene glycol, polypropylene glycol and 1,6-hexanediol. Thus, it appears that water soluble 1,3-alkyldiols and particularly 2-alkyl-1,3-alkanediols and 1,3-alkanediols are effective.

EXAMPLE I

An alkaline permanent wave solution containing four percent of 2-ethyl-1,3-hexanediol has been developed which reproducibly processes all normal to resistant hair types in five minutes at 50° C. or salon dryer temperatures. The hair so treated is in excellent condition and has a very tight long-lived curl pattern.

The solution is set forth in the following table. The ingredients other than the 1,3-diol are conventional ingredients in permanent wave solutions and the proportions are in conventional ranges. The Versenex 80 chelating agent comprises the pentasodium salt of diethylenetriaminepentaacetic acid available from Dow Chemical Company, Midland, Michigan. EDTA and its salts are also suitable chelating agents for sequestering metal ions in a water used to make the solution and in water applied to the hair. The Ameroxal OE-20 nonionic surfactant is a polyethylene glycol ether of oleyl alcohol available from Amerchol Chemicals, Edison, New Jersey. A variety of other surfactants are suitable for use in permanent wave solutions. The amount of aqua ammonia is approximate, as required to obtain pH 9.2.

TABLE

| Example I | |
|---|---|
| Component | % by weight |
| Ammonium Thioglycolate | 7.0% |
| Monoethanolamine Thioglycolate | 2.0% |
| Chelating agent (Versenex 80) | 0.25% |
| Nonionic Surfactant (Ameroxal OE-20) | 6.0% |
| Aqua Ammonia | 0.85% |
| Fragrance | 0.25% |
| 2-Ethyl-1,3-Hexanediol | 4.0% |
| Water | q.s. 100% |

Generally speaking, alkaline permanent wave solutions having free ammonia in the reducing solution are not processed with the addition of heat due to the tendency of such products to be irritating to the skin and damaging to the hair. The presence of 2-ethyl-1,3-hexanediol accelerates the cleavage reaction of the hair fibers' cystine disulfide linkages and provides a sparing effect on the hair fiber itself. In addition, the presence of the 1,3-alkyldiol stimulates the efficiency of curl formation. This permits processing of the hair with this solution in as little as five minutes and permits the application of heat despite the presence of ammonia.

EXAMPLE 2

A neutral permanent wave solution using ammonium thioglycolate (ATG) as the waving agent employs five percent of 2-ethyl-1,3-hexanediol. The nonionic surfactant mentioned in the following composition, Brij 35, is a polyoxyethylene ether of an aliphatic alcohol available from ICI United States, Inc., Wilmington, Del. The amount of monoethanolamine is approximate as required to adjust the pH to 7.0.

TABLE

| Example 2 | |
|---|---|
| Component | % by weight |
| ATG | 12% |
| Chelating Agent (Versenex 80) | 0.5% |
| Nonionic Surfactant (Ameroxal OE-20) | 6.0% |
| Fragrance | 0.3% |
| Monoethanolamine | 1.6% |
| Nonionic Surfactant (Brij 35) | 1.0% |
| 2-Ethyl-1,3-Hexanediol | 5.0% |
| Water | q.s. 100% |

This solution can be used for permanent waving even though ATG is a poor nucleophile at pH 7.0, with efficiency at least as good as a neutral permanent waving solution employing the more expensive glycerol monothioglycolate.

EXAMPLE 3

An exemplary acid solution having a pH of 4.1 has the following composition:

| | |
|---|---|
| cysteamine | 8.97% |
| 2-ethyl-1,3-hexanediol | 4.0% |
| Ameroxal OE-20 | 5% |
| Versenex 120 | 0.5% |
| Brij 35 | 1.0% |
| Fragrance | 0.3% |
| Water | q.s. 100% |

This solution had a pH of 4.1. It was tested in the standard curl efficiency test, processing the hair for five minutes at 50° C. An efficiency of 72 to 75% was observed. Thus, there is provided both a fast and an acid permanent wave composition. This is particularly surprising since, in the absence of the 1,3-alkyldiol the beta-mercaptoethylamine is not useful at all at this pH.

Another surprise with this material is that the pH can be raised with ammonia to make an acceptable alkaline permanent wave solution. By adding 4.27% of 28% aqua ammonia, the pH is raised to 9.2 to 9.5. This solution is also quite satisfactory as a permanent wave composition. This combination of ingredients is not completely insensitive to pH since it is not commercially practical in a pH range of from about 6.5 to 7.5. Thus, this composition is appropriate when the pH is in the range of from 3 to 6.5 or from 7.5 to 9.5. The cysteamine has been known for its ability to cleave the interprotein bonds, but has not been previously used in commercial hair waving solutions since not readily available. It is safe and non-toxic and now more readily available, giving it excellent prospects as a commercially important composition.

Although limited embodiments of permanent wave solutions containing 1,3-alkyldiols have been specifically described herein, it will be apparent that other compositions may be provided in practice of this invention. As is particularly apparent from Table IV and the examples, the 1,3-alkyldiol enhances a broad variety of conventional aqueous permanent wave solutions for use under a variety of salon conditions. Many other conventional materials not specifically mentioned may also be included in the permanent wave solutions, such as for example, thickeners, combing aids, cosmetic ingredients, colors, conditioners and the like. It is therefore to be understood that within the scope of the appended claims, this invention may be practiced otherwise than as specifically described.

What is claimed is:

1. An aqueous permanent wave solution comprising:
    at least one compound for cleaving interprotein disulfide bonds in hair selected from the group consisting of thioglycolates, thiolactates, mercapto compounds and thioglycerol; and
    at least one biocompatible 1,3-alkyldiol in the range of from 2 to 7% by weight.

2. A solution as recited in claim 1 wherein the 1,3-alkyldiol is selected from the group consisting of 2-alkyl-1,3-alkyldiols and 1,3-alkyldiol.

3. A solution as recited in claim 1 wherein the 1,3-alkyldiol comprises 2-ethyl-1,3-hexanediol.

4. A solution as recited in claim 1 wherein the 1,3-alkyldiol comprises 1,3-butanediol.

5. A solution as recited in claim 1 wherein the 1,3-alkyldiol is present in the range of from 4 to 6% by weight.

6. A solution as recited in claim 1 wherein the pH of the solution is about 7.

7. A solution as recited in claim 1 wherein the pH of the solution is in the range of from 3 to 6.5.

8. A conventional aqueous permanent wave solution containing an active ingredient selected from the group consisting of thioglycolates, thiolactates, mercapto compounds and thioglycerol, and characterized by inclusion of 2-ethyl-1,3-hexanediol in the range of from 2 to 7% by weight.

9. A solution as recited in claim 8 wherein the 2-ethyl-1,3-hexanediol is present in the range of from 4 to 6%.

10. A conventional aqueous permanent wave solution containing an active ingredient selected from the group consisting of thioglycolates, thiolactates, mercapto compounds and thioglycerol characterized by inclusion of 1,3-butanediol in the range of from 2 to 7% by weight.

11. A solution as recited in claim 10 wherein the 1,3-butanediol is present in the range of from 4 to 6%.

12. A permanent wave solution comprising:
    ammonium thioglycolate in the range of from three to twelve percent by weight; and
    a 1,3-diol selected from the group of 2-ethyl-1,3-hexanediol and 1,3-butanediol in the range of from 2 to 7% by weight.

13. A solution as recited in claim 12 wherein the pH is about 7.

14. A permanent wave solution comprising:
    at least one compound for cleaving interprotein disulfide bonds selected from the group consisting of salts of thioglycolic acid, esters of thioglycolic acid and salts thereof, salts of thiolactic acid, mercapto compounds, and thioglycerol; and
    a 1,3-alkyldiol in the range of from 2 to 7% by weight; and
    having a pH in the range of from 3 to 9.5.

15. A solution as recited in claim 14 wherein the 1,3-alkyldiol is selected from the group of 2-ethyl-1,3-hexanediol and 1,3-butanediol.

16. A solution as recited in claim 14 wherein the compound for cleaving interprotein disulfide bonds is selected from the group consisting of ammonium thioglycolate, monoethanolamine thioglycolate, glycerol monothioglycolate, ammonium lactate, monoethanolamine thiolactate, beta-mercaptoethylamine, and thioglycerol, in the range of from three to twelve percent by weight.

17. A permanent wave solution comprising:
    beta-mercaptoethylamine; and
    a 1,3-alkyldiol in the range of from 2 to 7% by weight; and
    having a pH in the range of from 3 to 6 or in the range of from 7.5 to 9.5.

18. A solution as recited in claim 17 wherein the 1,3-alkyldiol is selected from the group consisting of 2-ethyl-1,3-hexanediol and 1,3-butanediol.

19. A permanent wave solution comprising:
    monoethanolamine thioglycolate in the range of from three to twelve percent by weight; and
    a 1,3-diol selected from the group of 2-ethyl-1,3-hexanediol and 1,3-butanediol in the range of from 2 to 7% by weight.

20. A permanent wave solution comprising:

glyceryl monothioglycolate in the range of from three to twelve percent by weight; and
a 1,3-diol selected from the group of 2-ethyl-1,3-hexanediol and 1,3-butanediol in the range of from 2 to 7% by weight; and
having a pH in the range of from 7 to 8.

21. A permanent wave solution comprising:
ammonium thioglycolate plus monoethanolamine thioglycolate in the range of from three to twelve percent by weight; and
a 1,3-alkyldiol selected from the group of 2-ethyl-1,3-hexanediol and 1,3-butanediol in the range of from 2 to 7% by weight.

* * * * *

UNITED STATES PATENT AND TRADEMARK OFFICE
CERTIFICATE OF CORRECTION

PATENT NO. : 4,963,349

DATED : October 16, 1990

INVENTOR(S) : R.A. Mathews; E.R. Moore; D.W. Cannell

It is certified that error appears in the above-identified patent and that said Letters Patent is hereby corrected as shown below:

Column 7, line 64, change "1,3-alkyldiol" to
-- 1,3-alkanediols --.

Column 8, line 28, after "from 2" delete the semicolon.

Signed and Sealed this

Twenty-sixth Day of May, 1992

Attest:

DOUGLAS B. COMER

*Attesting Officer*

*Acting Commissioner of Patents and Trademarks*